United States Patent
Ahlers et al.

(10) Patent No.: US 6,200,444 B1
(45) Date of Patent: Mar. 13, 2001

(54) CATION-SELECTIVE SENSOR

(75) Inventors: Benedikt Ahlers; Alexandre Choulga; Karl Cammann, all of Muenster (DE)

(73) Assignee: Institut fuer Chemo und Biosensorik Muenster e.V. (DE)

( * ) Notice: Subject to any disclaimer, the term of this patent is extended or adjusted under 35 U.S.C. 154(b) by 0 days.

(21) Appl. No.: 09/155,510

(22) PCT Filed: Mar. 27, 1997

(86) PCT No.: PCT/DE97/00645

§ 371 Date: Nov. 25, 1998

§ 102(e) Date: Nov. 25, 1998

(87) PCT Pub. No.: WO97/37215

PCT Pub. Date: Oct. 9, 1997

(30) Foreign Application Priority Data

Mar. 29, 1996 (DE) .............................. 196 12 680

(51) Int. Cl.$^7$ .................................. G01N 27/26
(52) U.S. Cl. ............................ 204/418; 204/416
(58) Field of Search ............... 422/82.01, 82.02; 204/417, 418, 419, 416; 324/438, 439

(56) References Cited

U.S. PATENT DOCUMENTS 5,312,762  5/1994  Guiseppi-Elie .
5,964,994 * 10/1999  Craig et al. ..................... 204/418

FOREIGN PATENT DOCUMENTS 677 295      4/1991  (CH) .
42 41 438 C2 6/1995  (DE) .
93 06237     4/1993  (WO) .

OTHER PUBLICATIONS

CAPLUS abstract of Sun et al. (Synthesis of fluorinated fluoresceins, J. Org. Chem. (1997), 62(190, 6469–6475), 1997.*
CAPLUS abstract of Wolfbeis et al. ("A new group of fluorescent pH–indicators for an extended PH–range", Fresenius'Z. Anal. Chem. (1987), 32793–4), 347–500, 1987.*
CAPLUS abstract of Ulrike et al. ("Surface charge of bacteriorhodopsin detected with covalently bound pH indicators at selected extracellular and cytoplasmic sites", Biochemistry (1994), 33(1), 298–306), 1994.*
N.F. Sheppard, JR., M.J. Lesho, P. McNally, and A.S. Francomacaro; "Microfabricated conductimetric pH sensor"; Sensors and Actuators B; vol. B28, No. 2, 1995, pp. 95–102.
A.A. Shul'GA, B. Ahlers, and K. Cammann; "Ion–selective conducto–metric microsensors based on the phenomenon of specific salt extraction"; Journal of Electroanalytical Chemistry, vol. 395, Nos. 1 and 2, 1995, pp. 305–308.
Patent Abstracts of Japan, vol. 11, No. 43, Feb. 7, 1987, and Japanese 61 207443 A, Sep. 13, 1986.

* cited by examiner

*Primary Examiner*—T. Tung
*Assistant Examiner*—Alex Noguerola
(74) *Attorney, Agent, or Firm*—Marshall & Melhorn

(57) ABSTRACT

The invention concerns a cation-selective sensor provided with a cation-selective coating and based on the fact that analyte ions present in a solution cause detectable changes in the electrical characteristics of the layer. The acid/base components in the cation-selective layer render the sensor function independent of the anions present in the analyte solution. This improves the measurement accuracy and lowers the detection threshold.

27 Claims, 4 Drawing Sheets a)

b)

A-A

CATION-SELECTIVE SENSOR

BACKGROUND OF THE INVENTION

1. Field of the Invention

The invention relates to a cation-selective sensor which has a cation-selective coating. As a result of cations to be detected coming into contact with this layer, a detectable change in the electrical properties of the layer is brought about.

2. Description of the Prior Art

For the determination of ions in solutions, use is frequently made of the potentiometric ion-selective electrode (Cammann, K., Die Arbeit mit Ionenselektiven Elektroden [Working with ion-selective electrodes], 2nd ed., Springer Verlag: Berlin, Heidelberg, New York, 1977). Ion-selective electrodes are electrochemical sensors with which the concentration or activity of specific ions can be determined by means of a potential difference. The ion-selective potential difference occurs at the phase boundary between active electrode material/electrolyte and depends according to the Nernst equation on the activity of a specific ion in the solution. One example of sensors of this type are ion-selective field-effect transistors (for example DE 29344005 C2).

Unlike the case of resistance and capacitance, the absolute values of the electrical potential have no physical meaning, since the potential can only be defined in relation to a reference value. In electrochemistry, such a reference value is customarily given by the potential of the reference electrode. The need for a reference electrode is the critical disadvantage with the use of potentiometric measurements for the determination of ion activities in solution.

Another fundamental limitation with the potentiometric analysis methods relates to the composition of the ion-selective membrane. The requirements made of the nature of the specific binding and/or of the complexing sites within the membrane should be such that the potential difference at the membrane/solution interface is generated selectively as a function of the presence of a particular species in the solution. For example, this binding should not be too strong, in order to permit sufficiently fast exchange of the detected species between the membrane phase and the solution.

Besides the potentiometric analysis methods, the most frequently used electrochemical analysis methods are those which measure the current through a suitably prepared or modified conducting or semiconducting working electrode. The potential of this electrode is set by that of the reference electrode. The measured current results from the electrochemical redox reaction which takes place at the working electrode/solution interface. In addition to the reference electrode which is needed, the use of this measurement method is further limited by the fact that the measured species must be electroactive at the working potential applied to the working electrode. Furthermore, this potential must be different from that of the interfering species. The latter point often causes a problem since many chemical compounds or large groups of chemical compounds have very similar redox properties. In addition, the required electrode potentials for many compounds lie outside the range which is practically usable.

The non-electrochemical methods usually employed for the specific recognition of charged and neutral species include the various types of liquid chromatography. In this case, the sample to be analysed is brought into contact with a so-called stationary phase, for example a polymer layer, which specifically binds or retains the detected species. The strength of this binding determines the retention time of the analyte within the chromatography column. When tailor-made stationary phases are used, very many species can be identified. However, this type of analytical measurement arrangement is highly complex and very expensive.

A further possibility for the determination of ions in solutions is given by ion-selective optodes. Ion-selective compounds and indicators, which contain structural elements that change their optical properties in the UV/VIS range, can be used as chromoionophores and fluoroionophores in corresponding ion-selective sensors with optical signal transmission. An overview of the way in which ion-selective optodes function is given in the following articles: K. Seiler, Ionenselektive Optodenmembranen [Ion-selective optode membranes], Fluka Chemie AG, Buchs, Switzerland (1991), ISBN 3-905617-05-6, W. Morf, K. Seiler, P. P. Sörensen, W. Simon, Ion-Selective-Electrodes, Vol. 5, Pergammon Press, Oxford, New York, Akademiai Budapest (1989), p. 141.

Interaction of ions with the chromophore components, or fluorescent components, in a membrane which is applied to an optical transducer system, leads to absorption or excitation of the fluorescence, and it has in this way been possible to develop chemical sensors for colourless or non-fluorescent substances.

The optical sensor systems have fundamental disadvantages. For example, the optical systems are disturbed by background light and, compared with electrochemical sensors, have relatively narrow dynamic measurement ranges. Furthermore, the long-term stability of immobilized components is limited by photolytic breakdown and leaching, and the response times of optical sensors are relatively long. Further disadvantages of ion-selective optodes include incompatibility with microelectronics and the lack of possibilities for integration.

The synthesis of chromophore compounds or fluorescent compounds is very time-consuming and cost-intensive, which is likewise highly disadvantageous.

A further possibility for the determination of ions in solutions is given by test rods and test papers. This involves a microchemical investigation method, in which chemical reactions, visible to the naked eye, of small quantities of elements (in the form of their ions) or compounds can be identified. The analytes can be identified by virtue of their colour reactions (colour changes). In this case, all the reagents needed for the specific detection reaction are applied to a support and, on exposure to an aqueous analyte solution, the analyte in question can be assigned to a concentration range according to the intensity or the hue of the respective coloration. The reagents used in test papers and test rods for the specific colour reactions or colour changes are also used in colorimetric test systems. In colorimetry, the colour intensity of a sample solution is visually compared with the intensity of standard solutions whose concentrations are known. Problems and disadvantages are found with the accuracy in these determination methods, which often only give semiquantitative conclusions. It is not possible to use test strips in on-line measurement systems, and so test strips cannot function as sensors. EP 0 153641 A2 presents the structure and measurement method for some test strips.

Another important class of analytical methods for the detection of charged or uncharged species in a gas or liquid medium employs the measurement of resistance or capacitance. Variations in the conductance or the dielectric properties of a layer of a sensitive material are exhibited as a function of the interactions with the detected species. In the field of gas detection, resistive and capacitive sensors are thus widely used.

In contrast to this, the use of such sensors is encountered only infrequently for chemical analyses in liquids. Measurements of the total conductance of electrolyte solutions are of only limited analytical meaning, because they generally lack specificity. Notwithstanding, in GB 2204408 A, R. S. Sethi et al. described a conductimetric enzyme biosensor which has finger-like interdigital electrodes (IDEs) that are covered by a membrane of immobilized urease. When urea is present in the test solution, the use of densely arranged electrodes makes it possible to measure the conductance of the solution with which the enzyme layer is saturated, so long as the conductance changes specifically with respect to the urea hydrolysis which is catalysed by urease. The shortcomings of biosensors of this type includes the drastic reduction in the sensitivity of the biosensor as the buffering capacity and/or ion strength (conductance) of the solution increases.

WO 93/06237 describes the use of IDEs for measuring the change in conductance of a layer of electroactively conducting polymer (polyaniline, polypyrrole). These changes result from the interaction of the functional redox groups of the polymer with the species of interest present in the solution, or with species which result from an enzymatic reaction in the layer of immobilized enzyme which is applied to the top of the layer of the said polymer.

U.S. Pat. No. 4,334,880 describes an analyte-specific resistance meter, an electrically conducting or semiconducting layer of polyacetylene being used as an analyte-specific layer.

In GB 21 37 361, L. S. Raymond et al. describe a capacitive detection arrangement which contains the following components:

1. a capacitor consisting of two IDEs;
2. a first layer of electrically insulating material, which covers the electrically conducting electrode and shields it from the solution to be analysed;
3. a second layer of a material, which covers the first layer, the second layer being permeable to a specific non-aqueous substance in a solution, which, through its entry into the electric field between the IDEs, causes a change in the capacitance of the capacitor.

The second layer contains, for example, valinomycin which is selectively permeable to potassium ions. The interdigital electrodes measure the changes in the capacitance as a result of the specific uptake of ions into the valinomycin layer.

GB 21 37 361 does not give any description of the membrane composition, that is to say there is a lack of indication as to the conditions needed to ensure the required permeability of the sensitive second layer in relation to the species of interest. In addition, conditions of this type greatly limit the number of species that can be detected. The need to shield the conducting electrodes with an insulating layer makes it more difficult to produce the transducer on account of the stringent requirements for the quality of a layer of this type, and at the same time worsens the sensitivity of the sensor. A further problem is that it is not possible to rule out an abrupt change in the dielectric constants of the measuring layer as a function of the composition of the solution to be analysed.

SUMMARY OF THE INVENTION

On the basis of the disadvantages of the prior art which have been presented, the object of the present invention is to propose a novel sensor design and corresponding sensors which make it possible for cations contained in solution to be determined quantitatively and/or qualitatively by means of an absolute measurement, without the use of reference electrodes, and at the same time to avoid interference by anions, so as to increase the measurement accuracy and lower the detection limit.

This object is achieved by the characterizing features of claim 1. The subclaims present advantageous refinements.

The invention proposes the use of an impedimetric cation-selective sensor which consists of at least one ionically conducting cation-selective layer (membrane) which is in contact with the solution and is made of a liquid, semi-solid or solid material. This layer is connected to at least one of at least two electrodes. The electrodes may be applied to a support.

The components of the cation-selective layer should be immiscible with the solution, so that the layer does not "bleed". Use is preferably made of an aqueous solution and a lipophilic cation-selective layer. In this case, the hydrophobic material contains at least one hydrophobic substance which is immiscible with the aqueous solution, can be used as a matrix and/or solvent for further layer components and contains coupling elements that recognize cations.

According to the invention, it is also proposed that the layer contain functional groups and/or compounds which can function as acid/base in protonatable form. They may be present in the layer, for example, in the form of a pH indicator or a lipophilic acid or base. Through selection of the measurement conditions, the acid/base component is in protonated form in the membrane.

The proposed novel layer composition permits an entirely new mode of operation of impedimetric cation-selective sensors. When the sensors according to the invention are in contact with the solution to be analysed, ion exchange takes place between the cation-selective layer and the solution. The cations which are to be detected and are contained in the solution enter the cation-selective layer and form complexes with the selective coupling elements present in the layer. At the same time, in order to maintain charge neutrality for the layer, protons which are bound to acid or base functional groups in the layer leave the cation-selective layer and enter the solution. On account of the acid/base component according to the invention in the cation-selective layer, there is thus no need for additional take-up of anions from the solution (anion coextraction) for the required charge compensation.

This is advantageous since it is never exactly known which anions in detail, and in what quantities, enter the selective layer from the solution in order to compensate for the charge of the cations, would thus affecting the sensor properties. This problem is particularly serious in the analysis of biological samples and physiological fluids, in which the presence of a large number of different highly lipophilic anions has long been known. By avoiding anion interference, the acid/base component present in the cation-sensitive layer thus ensures, at the same time, a high measurement accuracy and a low detection limit for the sensor.

The bulk electrical properties of the layer change because of the described ionic processes, and this can be detected using electrodes in contact with the layer. In this case, it is not of critical importance whether reversible or irreversible cation uptake in the cation-selective layer takes place, since the measurements of the layer properties, for example resistance or conductance, are absolute measurements. In the case of irreversible cation extraction, or binding, the sensor according to the invention can be used as a dosimeter, that is to say the change in the electrical properties of the membrane can be regarded as a cumulative parameter ("dose") of the analyte traces in a medium to which the measuring arrangement is exposed over a fairly long period of time.

The cation-selective sensors according to the invention have the following advantages over the prior art:

1. No reference electrode is needed in the sensors according to the invention, since the measurements of electrical properties such as conductance or admittance are, in contrast to e.g. potential measurements in potentiometry, absolute measurements.
2. The novel functional mechanism of the sensor avoids the interfering effect of ions in the sample solution on the response of the sensor.
3. The use of ion exchange as a novel functional mechanism for the sensor improves the response of the sensor (reversibility, selectivity, stability).
4. A wide range of new materials can be used for sensor optimization and sensor production.
5. The novel functional mechanism of the sensor greatly suppresses the effect of the sample matrix on the measurement results, and substantially facilitates the sample preparation.
6. In contrast to potentiometric sensors, these sensors allow the determination of analyte concentrations in solutions with very high ion strength.
7. With the sensors, it is possible to measure the solution composition in closed vessels, for example in sealed glass ampoules, using contactless measuring techniques.
8. The sensors can be designed as complete solid-state systems with a high level of integration. This allows extensive miniaturization and ensures compatibility with microelectronics.

The conductive materials used to produce the solid or semi-solid or porous measuring electrodes are substances which, on account of the mobility of electrons or holes, exhibit the properties of an electrical conductor, a semiconductor or a p-type conductor. Examples of these include:

noble metals (Ag, Au, Pt, Pd, . . . );
other metals with sufficient chemical stability (Ni, Ta, Ti, Cr, Cu, V, Al, . . . );
conductive pastes and epoxy resins containing metal particles or graphite particles;
carbon-based materials (carbon fibres, glassy carbon, graphite);
heavily doped silicon (poly-Si);
conductive polymers (polypyrrole, polyaniline, polyacetylene, . . . );
conducting polymers which contain metal particles or graphite particles.

The conductors may be self-supporting, for example in the form of rods, wires or meshes, or may be embedded in plastic or another insulating support in such a way that only the membrane contact face is left free. This exposed part may, for example, be present in the form of discs or bands.

As an alternative to this, the conductors may also be formed on an insulating support in the form of thick or thin films (the expressions refer to the established use of the expressions thick-film and thin-film technology in the field of microelectronics). Production may, for example, be carried out using screen printing, by chemical or electrochemical polymerization or deposition (the latter in the case of metals), by vacuum evaporation, sputtering or other techniques in thick- and thin-film technology. The conductors applied to an insulating support may, for example, be present in the form of bands, circles, discs or interdigital electrodes. The conductors may be arranged on the same or on opposite sides of the support, in a plane or vertically separated from one another.

The surface of the measuring electrode need not necessarily be smooth or polished. It may be roughened in order to produce better contact with the cation-selective layer and in order to reduce the interfacial resistance.

Furthermore, for the case when high electrochemical boundary resistances occur between the conductors and the layer, an additional layer, made of substances forming redox pairs, may be arranged between the conductors and the analyte-selective layer in order to suppress the interfacial resistance. Substances of this type which form redox pairs and suppress interfacial resistance are described in CH 677 295. Reference is therefore expressly made to the content of the disclosure. The thickness of the layer is typically in the range from 0.01 $\mu$m to 100 $\mu$m.

Since no electron transfer between the electrodes and the analyte-specific layer is necessary during AC measurements, direct contact between the surface of the conductor and the layer is not necessary. It is therefore possible to take measurements of this type, using capacitive coupling, with electrodes which are separated from the analyte-selective layer by an air gap or insulating layer. It is likewise possible to use inductive coupling for contactless measurements of the electrical properties of layers. In this case, the layer is placed in a coil through which a current then flows. Eddy currents are created in the layer and cause a power loss as a function of the layer conductance. A further possibility consists in the use of two coils which are connected by a current loop in the sample.

Further suitable electrode arrangements and relevant modifications are given in DE 44 37 274.4-52.

The cation-specific layer according to the invention, which contains cation-selective coupling elements and components with acid/base properties, may have a variety of compositions and consistencies. According to the invention, the layer material may, for example, consist of organic liquids, polymers or ion exchangers, as well as combinations of these components.

Liquids which may be used as the coating material will be considered first, corresponding mixtures also being envisageable. The following liquids may be mentioned by way of example: non-polar solvents such as tetrachloromethane, chloroform, hexane, toluene and most unsaturated aromatic hydrocarbons.

The cation-selective layer may contain one or more plasticizers. Plasticizers are liquid or solid inert organic substances with low vapour pressure, predominantly those of the ester type. They are capable, without chemical reaction, primarily through their solvent and/or swelling power, although possibly even without this, of chemically/ physically interacting with highly polymerized materials and forming a homogeneous system with them [DIN 55945 (December 1988)]. Use is preferably made of plasticizers which have lipophilic properties.

An extremely wide variety of plasticizers may be used, for example phthalates, trimellitates, aliphatic discarboxylates, sebacates, polyesters of adipic, sebacic, azelaic and phthalic acids with diols such as 1,3-butanediol, 1,2-propanediol, 1,4-butanediol etc., phosphates, fatty acid esters, hydroxycarboxylates, epoxidized fatty acid derivatives, in particular triglycerides and mono-esters, polyamide plasticizers, for example benzenesulphonamides or p-toluenesulphonamides, or long-chain aliphatic alcohols.

Mixtures of two or more plasticizers may also be added in order to plasticize the receptor layers.

The use of plasticizers of this type in ion-selective membranes is described in the literature. The following plasticizers, having lipophilic properties, may be cited by way of example: ethers, for example o-nitrophenyl octyl ether, ester/amide plasticizers, in this case particularly dicarboxylic acid diester plasticizers and tetracarboxylic acid tetraester plasticizers, the esterifying component being an aliphatic alcohol, generally having at least five carbon atoms, for example bis(2-ethylhexyl) sebacate, and diesters of phosphoric acid or phosphonic acid.

Many plasticizers are oxygen donors having further functional groups, for example: bis(2-ethylhexyl) sebacate, dioctyl phthalate, dibenzyl ether, tris-2-ethylhexylphospshates etc.

According to the invention, one or more polymers, preferably immiscible or only slightly miscible with aqueous solutions, may be considered as components of the cation-specific layer.

Thus, mention may be made of polymers which form the polymer matrix on the transducer, that is to say on the electrodes and the optional support. Homopolymers or copolymers which result from alkene monomer units and optionally have non-polar or weakly polar substituents:

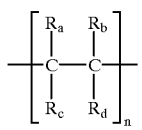

Examples of the substituents $R_i$ which may be mentioned include: $R_i$=—H, —F, —Cl, —Br, —NO$_2$, —COR, —SH, —CN, —COOR (bound to the main polymer chain via the oxygen atom or carbon atom), carbonitrile groups, carboxyamide groups, aliphatic/aromatic ether groups, and aromatic/heteroaromatic radicals. The composition of the polymer material may range from low molecular weight to very high molecular weight, but high molecular weight is preferred.

Among the aforementioned homopolymers or copolymers based on monomer units, which originate from alkenes, those especially preferred are one which are a vinyl halide or vinylidene halide homo- or copolymer. In these homo- or copolymers the halogen atom is preferably a chlorine atom.

Furthermore, the following other polymer materials (and corresponding homo- or copolymers or derivatives) may also be considered for the polymer matrix of the solid or semi-solid membrane: polyvinyls, such as polyvinyl chloride, polyvinyl stearate or polyvinyl acetate polymethacrylate, cellulose derivatives such as cellulose ester and cellulose ether, polyethylene oxides, polyamides, polyimides, polyesters, polyethers, polyphenols, polystyrenes, polyurethanes, polycarbonates, polypyrroles, polyanilines, polyacetylenes, polysiloxanes, silicon-containing polymers such as silicones, halogenated silicones or silanes, polyacroleines, polyacrylics, polyacrylonitriles, polyethylenes, halogenated polymers, polyenes, polyethylene glycols, polyglycols, polyureas, polyisocyanates, polyisocyanides, polyisoprenes, polyketones, polymaleic acid (derivatives), polysaccharides, polyols, polypeptides, polyphenylene, polypropylenes, lignin or chitin.

It is likewise possible for modified copolymerized polymers or polymer mixtures of two or more polymers or copolymerized polymers to be used as a constituent of the cation-selective layer.

According to the invention, the hydrophobic material may consist of a combination of polymers and plasticizers.

Layers made of polymers may contain organic, lipophilic, water-insoluble liquids, preferably ethers and esters of aliphatic alcohols. The selectivity of the hydrophobic layer can be modified by changes in the layer composition and constitution of the individual components.

The cation-selective layer may also contain a porous matrix/support (for example filter paper, fabric, microporous glass, ceramic) for stabilizing the other components. The use of a porous matrix/support furthermore leads to homogenization of the individual components.

The cation-selective coupling elements are an essential constituent of the cation-selective layer. In the context of the invention, the term coupling elements is intended to mean all compounds or radicals and functional groups which are capable of binding or complexing the cations contained in the solution to be investigated.

The cation-specific layer may, on the one hand, consist of liquids and/or polymers which themselves have corresponding coupling elements for the selective extraction of cations. On the other hand, however, it is also possible for the layer as described above to contain polymer materials and/or organic liquids, and for cation-selective coupling elements to be added additionally.

The cation-selective coupling elements are capable of selectively forming complexes with cations from an aqueous sample solution which is in contact with the cation-selective layer, and therefore of specifically taking up cations from the solution into the layer.

According to the present invention, the term cation-selective coupling elements should be taken to mean, amongst others, functional groups, ion exchangers, complexing groups, or chelating groups, clathrates (for example podands, coronands, polyethers, cyclophanes, crown ethers, antibiotics, cyclodextrins), natural and synthetic polypeptides, lipids and surfactants.

The coupling elements may be complexing plasticizers, or plasticizers that can form chelates. They contain corresponding chelating functional groups covalently bonded to the plasticizer. Complexing of these groups with ions may take place both intramolecularly and intermolecularly. Examples which may be mentioned at this point include plasticizers such as cis-N,N,N-tetraisobutyl-1,2-cyclohexanedicarboxamide and dioctyl phosphonate as Li$^+$-selective plasticizers.

The cation-specific layer may contain polymers having cation-selective coupling sites, which are capable of selectively extracting cations from the solution into the layer. The cation-selective layer is preferably an ionic conductor.

According to the invention, the polymers may be complexing polymers, for example polymer chelating agents. They contain corresponding chelating functional groups covalently bonded to polymers, which may be uncrosslinked or crosslinked. Complexing of these groups with ions may take place both intra- and inter-molecularly. Complexing groups (ligands) of customary complexing polymers are iminodiacetic-acid, hydroxyquinoline, thiourea, guanidine, dithiocarbamate, hydroxamic-acid, amidoxime, aminophosphoric-acid, (cycl.)polyamino, mercapto, 1,3-dicarbonyl, thio, cyano and crown-ether radicals, sometimes with very specific activities with respect to ions of different metals.

Base polymers of the complexing polymers are, besides polystyrenes, polyacrylates, polyacrylonitriles, polyvinyl alcohols, polyethylene imines and polysiloxanes. The complexing polymers are preferably produced in polymer-like reactions with crosslinked polyvinyl compounds.

Through polymer-like reactions, it is possible for complexing polymers to be obtained both from natural polymers, such as cellulose, starch, lignin or chitin, and from modified natural polymers, for example humic acid. The compounds may likewise be covalently bonded to the polymer such as clatherates (for example cyclophanes, crown ethers, antibiotics, cyclodextrins), natural or synthetic polypeptides, lipids and surfactants. Examples for polymers of this type include polysaccharides with active ligands, polycrown ethers, polycrown vinyls, polyether copolymers and polyacrylates, polysaccharides and polysiloxanes with active ligands.

Surfactants, colloidal gold, graphite, glass or inorganic microparticles or beads may, included in the polymer films, serve as molecular carriers.

The selective binding of neutral or charged species, for example alkali metal ions $Mg^{2+}$, $Ca^{2+}$ or transition metal ions, to specific functional groups in the polymer layer may cause a change in the morphology and pore size, to be precise (a) increase/decrease in the cross-linking of the matrix polymer, or (b) configurational molecular change in the components of the membrane layer.

Changes in the morphology may lead to a change in the electrical properties of the membrane layer, for example the ionic conductance. This is the case with some gels, proteins, especially receptor proteins, lipids and surfactants which contain functional groups that are capable of binding cations.

Use may likewise be made of polymer films which contain, covalently bonded to the basic polymer structure, ligands that enable cations to complex. These films may be crosslinked, for example by transition metal ions, if these ions form complexes or chelates with the ligands contained in the polymer at various sites on the polymer chain.

Cation-receptor polymer layers, for example multiphase polymer layers, which are sensitive to $Ca^{2+}$, may contain poly-L-glutamic acid chains in a block copolymer.

Among the molecules which are capable of causing configurational changes, induced by cation binding, mention may be made of polyions such as proteins and synthetic or natural polypeptides. Especially the two classes of polyanionic macromolecules, proteoglycans and acidic glycoproteins, exhibit the abovementioned characteristics, for example for sodium and calcium. These macromolecules represent polyanions, to be precise according to their carboxylated sialic or sulphate groups.

If the above-described polymer films contain dispersed conducting particles, contraction of the film causes an increase in the film conductance corresponding to the increased contact between the particles. The conducting particles preferably have a size of less than 10 $\mu$m, ideally less than 1 $\mu$m and consist, for example, of a semiconductor, metal or graphite.

The analyte-specific layer may have an ordered structure (that is to say the components of the medium form a liquid crystal phase), a partially ordered structure (for example the multi-double structures of films which are formed from polyionic complexes) or an amorphous structure. During the extraction of the analytes into the membrane phase, an effect on the conditioning of the membrane phase is possible, for example disorganization, as a result of which the bulk electrical properties are influenced.

The multi-double structures mentioned above may, for example, be formed from polyionic complexes between quarterery ammonium ions including surfactants and lipids and of polyions, for example polystyrene sulphonate and polyvinyl sulphonate. The components of a film of this type are, for example, dioctadecyldimethylammonium bromide ($2C_{18}N^+2CBr^-$) and sodium polystyrene sulphonate (PSS-$Na^+$).

The cation-specific layer may, further to the already mentioned polymer materials and/or liquids, additionally contain cation-selective coupling elements.

As complexing agents of this type, mention may preferably be made of complexing agents for cations which permit complexing as well as transfer mobility of cations in the hydrophobic cation-selective layer.

These complexing agents may have lipophilic properties and form charged complexes with cations. If appropriate, ion exchangers may likewise represent components in the layer, which give rise to the mobility of ions within the layer.

Many examples for above-described cation-selective components with lipophilic properties are described in the literature, and are used in ion-selective membranes in ion-selective sensors.

Examples of cation-selective components which may be mentioned here include cyclic complexing agents for cations, for example macrocycles such as crownethers (alkali selectivity), natural antibiotics (valinomycin-potassium selectivity, nonactin-ammonium selectivity) as well as non-cyclic, for example dicarboxylic acid amides (high selectivity with respect to alkali/alkaline-earth ions), tridodecylamine ($H^+$ sensitivity), coronades, podands, polyethers and cryptands.

Ion exchangers and ionic polymers may likewise be used as sensitive layer material in the context of the present invention, so long as the ion exchange with the detected ion results in a change of the electrical properties of the layer.

In this invention, the definition of an ion exchanger according to RÖMPP CHEMIE LEXIKON, Georg Thieme Verlag Stuttgart, 9th Edition, 1989, Vol. 3, pages 2026–2028 is used.

The characteristic feature of an ion exchanger and ionic polymer is the presence of a large number of hydrophilic groups which are bound to the polymer. These groups may be —$So_3H$ and —COOH, for example, in cation-exchange resins. Polymers of this type, for example persulphone polymers such as Nafion or Eastman Kodak AQ polymers, may also contain essential hydrophobic areas. Films are then formed with a heterogeneous structure, having separate hydrophilic and hydrophobic regions. A characteristic of these materials is the fact that, by the inclusion of water, they internally self-dilute and prevent local ionization, which results in a conductance close to that of aqueous electrolytes.

Examples of suitable ion exchangers include tetraalkyl ammonium salts, cationic metal complexes, dialkyl phosphates, tetraarylborates and salts thereof, for example tetraphenylborate and its silver and alkali metal salts, such as sodium tetrapheynylborate. The phenyl nuclei of the tetraphenylborate may be unsubstituted or substituted, preferably monochloro-substituted in the para position.

The term "ionic polymers" (definition according to RÖMPP CHEMIE LEXIKON, Georg Thieme Verlag Stuttgart, 9th Edition, 1989, Vol. 3, page 2038) relates, according to the present invention, to polymers which have basic or acidic functional groups bound onto or into the basic structure of the polymer. Examples which can function as ionic groups of ionic polymers include salts of sulphonic acid, phosphonic acid, carboxy, ammonium or phosphonium groups.

According to the invention, the ionomers forming the sensitive layer may in particular belong to the following groups: copolymers of ethylene, acrylic or methacrylic acid, carboxyelastomers, terpolymers, terpolymer, ethylenepropylenediene sulphonate, substituted polyvinyls such as polyacrylates, in particular polyacetates or butyrals or polyvinyl imidazols, perfluoropolymers, in particular perfluorosulphonates and polyampholytes.

In addition to the components and coupling elements so far described in the cation-selective layer, all the substances described in DE 44 37 274.4-52 may also be considered. Reference is expressly made to the entire content of the disclosure of DE 44 37 274.4-52.

The acid/base components according to the invention which are present in the cation-selective layer will be dealt with in more detail below. In the context of the invention, the term acid/base components is intended, amongst others, to mean functional groups and chemical compounds which, as a result of the release/take-up of cations to be detected in the cation-selective layer, function as proton donors/acceptors and can release or take up protons. On account of the coupling to other components of the cation-selective layer, or because of their own strong lipophilic nature, the acid/base components may preferably be imiscible or only slightly miscible with aqueous solutions.

The interaction of the cations to be detected with the cation-recognizing coupling elements existing in the layer, and the resultant proton take-up or release by the acid/base component in order to maintain charge neutrality, leads to a measurable change in the electrical properties of the cation-selective layer.

The measurement conditions and/or the composition of the selective layer are in this case chosen in such a way that the corresponding functional groups and chemical compounds having acid/base properties are preferably present in the cation-selective layer in protonate form.

The acid/base components preferably have an acid dissociation constant $pK_a$ in the range of from 3 to 12. Ideally, the acid/base component has a $pK_a$ of about 6 to 8.

According to the invention, account should be taken of the fact that each component of the hydrophobic material forming the layer may have functional groups which can function as acid/base in the layer.

The acid/base components existing in the selective layer may also preferably be represented by additionally added lipophilic acids or bases. pH indicators, for example, may function as lipophilic acid or base. They may be chemically modified correspondingly, so that they are suitably lipophilic. This modification may be carried out by the coupling of benzyl or other radicals, as well as by coupling one or more alkane chains with the chain length of preferably from 4 to 20 or more hydrocarbon atoms. Molecules suitable as pH indicators have been described in many standard works. Suitable examples thus include phenolic compounds such as p-nitrophenol or else compounds belonging to the category of indicators and their derivatives, such as compounds and derivatives of fluorescein, fluorescein esters, 7-hydroxycoumarin, resorufin, flavone or pyren-3-ol, or components such as 7-(n-decyl)-2-methyl-4-(3',5'-dichlorophen-4'-one)indo-naphthol (cf. also U.S. Pat. No. 493,951 and U.S. Pat. No. 493,981).

The choice of lipophilic acids or bases is not limited to pH indicators. Almost any functional groups and compounds which have the requisite proton donor/acceptor properties may, in the context of the invention, be used as an acid/base component according to the invention in the cation-selective layer, where appropriate after corresponding chemical modification.

Further examples of suitable categories of compounds include fatty acids, lipids and surfactants with weakly acid or basic properties.

Further components with acidic or basic properties may, for example, also be 9-(dimethylamino)-5-octadecanoylimino-5H-benzo[a]phenoxazine, 3-hydroxy-4-(4-nitrophenolazo)phenyloctadecanoate or corresponding derivatives.

In the context of the invention, the term acid/base component is also intended to mean a combination of several components (chemical compounds) whose reaction during interaction of the cations to be detected with cation-recognizing coupling elements present in the layer causes a measurable change in the electrical properties of the cation-selective layer.

The cation-specific layer may be applied to a support, for example to silicon with a passivation layer of $Si_3N_4$ or $SiO_2$, to glass, metal, ceramic, sapphire, plastic or polymer, in the form of films. The techniques for application of a polymer membrane layer are in this regard known from the prior art. Examples of suitable deposition methods which may be mentioned include precipitation from solution, dropwise application, dip coating, spraying, chemical, photochemcial or electrochemical polymerization, spin coating or photolithography.

The cation-selective layer preferably has the following proportions for the individual layer components:

20–80% by weight of polymer material, preferably 30–35% by weight

20–80% by weight of plasticizer, preferably 60–65% by weight

1–10% by weight of cation-selective coupling element, preferably 1–5% by weight

1–10% by weight of component with acid/base properties, preferably 1–5% by weight If appropriate, there is also a further component, for example an ion exchanger at 1–10% by weight, in the membranes.

In principal, all chemical compounds (plasticizers, polymers, ion exchangers, cation-selective complexing agents, ionophores, chromoionophores, lipophilic pH indicators and the like) which can be used according to the prior art for the production of potentiometric electrodes, ion-selective optodes or test strips, may also be used to produce the cation-specific polymer membrane layers proposed according to the invention. An overview of corresponding layer components can be found in the following sources: CRC Handbook of ion-selective electrodes: selectivity coefficients/Ed. Umezawa Y., CRC Press: Boca Raton, 1990; in product brochures, selectophores (ionophores for ion-selective electrodes and optodes) and quats, crowns and polyesters by the company Fluka Chemie AG; Vögtle F., Cyclophan-Chemie [Cyclophane Chemistry], Stuttgart: Teubner, 1990, etc.

The measurement conditions will now be explained in more detail. For analysis using the cation sensors proposed in this invention, it may possibly be necessary to match the pH of the aqueous sample to be analysed to a specific value. This is, in particular, relevant for water samples in industrial and environmental fields of application.

This matching may, for example, be done by diluting the sample with a buffer solution having a known pH, which represents a standard method of sample preparation. The buffer compositions and individual chemical components used for this are known from standard reference works. In general, water-soluble weak acids or bases, which can be found for example from Merck and Fluka company product catalogues, are used for the preparation of buffer solutions.

Examples which may be mentioned include the following buffers: tris(hydroxymethyl)aminomethane, N-bis-(2-hydroxyethyl)glycine, acetate/acetic acid, combined borate/citrate/dihydrogen phosphate buffer, etc.

Preferably, the pH of the aqueous sample solution should, as described above, be in the range of from 3 to 11, particularly preferably between 6 and 8.

For on-line analysis, the required sample preparation may be carried out by standardized addition of the conditioning buffer (conditioning solution).

According to the invention, the proposed ion sensors may be used as disposable sensors or as a type of test strip with electronic data acquisition. The sensor may, in this case, above the cation-selective layer, also have another layer which consists of dry soluble buffers, which if appropriate may be incorporated in a porous support matrix. The upper layer dissolves after contact with, for example, an aqueous solution, and this leads to the required adjustment of the pH of the sample solution.

If need be, the osmolarity (ionic strength) of the solution may also be matched to a standard value.

BRIEF DESCRIPTION OF THE DRAWINGS

Further details, features and advantages of the present invention are given by the following description of illustrative embodiments and with the aid of the drawings, in which.

DESCRIPTION OF THE PREFERRED EMBODIMENTS

Figure 1:
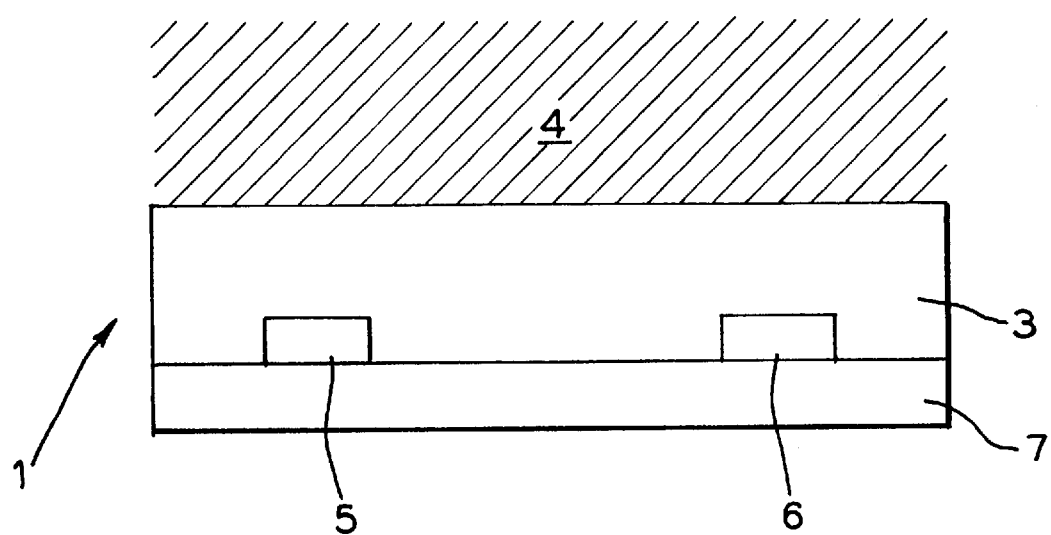
FIG. 1 shows the schematic structures of a first embodiment, of a cation-selective sensor with a cation-specific layer.

FIG. 1 shows a section of the schematic structure of a cation-selective sensor 1 according to the invention. The sensor 1 is in direct contact with the solution 4, and is in this case constructed in such a way that the analyte-specific layer 3 is applied to an inert support 7. The thickness of the sensitive layer 3 may in this case be in the range of from 0.01 $\mu$m to 1 mm. In the embodiment according to FIG. 1, the electrodes 5, 6 have direct contact with the layer 3. This layer has, in the illustrative case according to FIG. 1, the following composition:

64% by weight of polymer material

32% by weight of plasticizer

2% by weight of cation-selective coupling elements

2% by weight of components having acid/base properties

Figure 2:
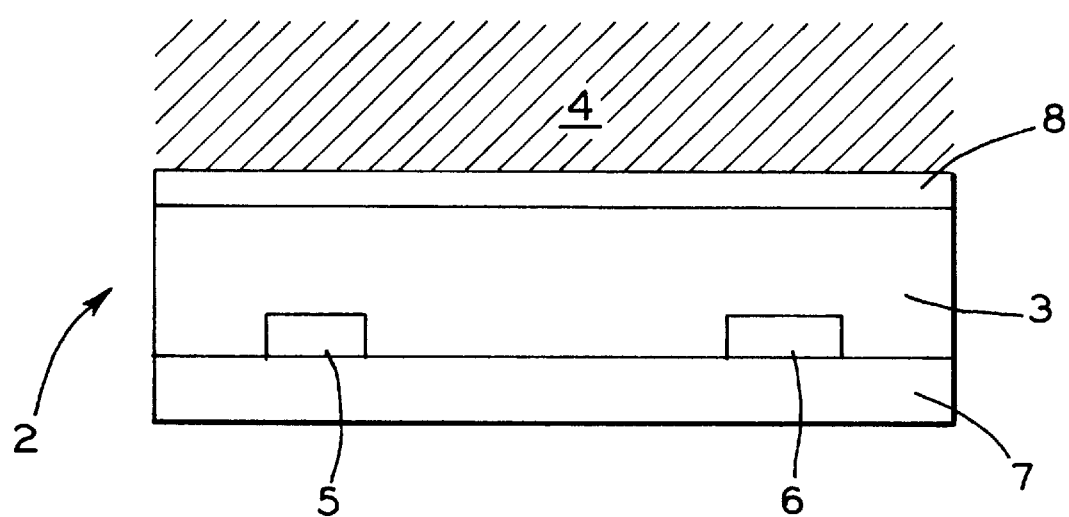
FIG. 2 shows the schematic structure of the second embodiment of a cation-selective sensor in the form of a test strip.

Next, FIG. 2 shows, in similar fashion to the illustrative embodiment according to FIG. 1, the schematic structure of a sensor according to the invention in the form of a test strip 2. In the illustrative embodiment according to FIG. 2, a further layer 8 is provided on the cation-selective layer 7. The layer 8 contains soluble suffer substances and optionally further components which are needed for the sample preparation. Following contact with an aqueous solution, the layer 8 dissolves, as a result of which the required adjustment of the pH value and, where appropriate, ionic strength of the sample solution takes place. In the illustrative case, the layer 8 consists of filter paper which contains the dried components of the phosphate buffer or TRIS buffer and has a layer thickness of from 0.01 $\mu$m to 1 mm.

Figure 3:
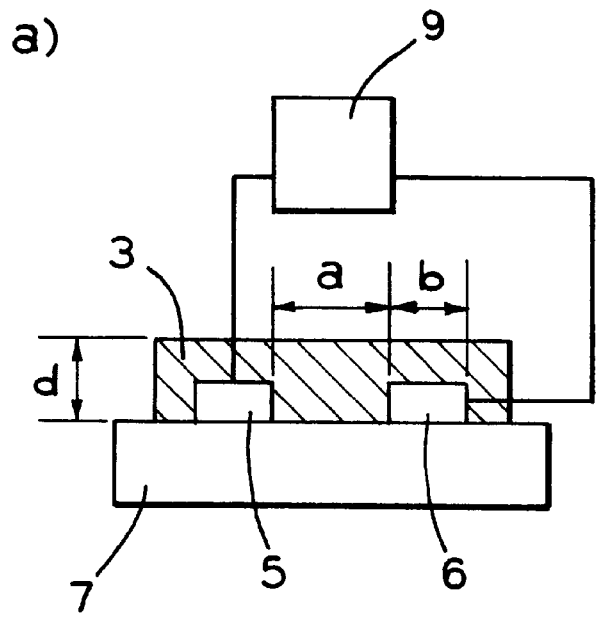
FIG. 3 shows examples of measuring-electrode arrangements, in which the conductors are produced in the form of thick or thin films.
Figure 3:
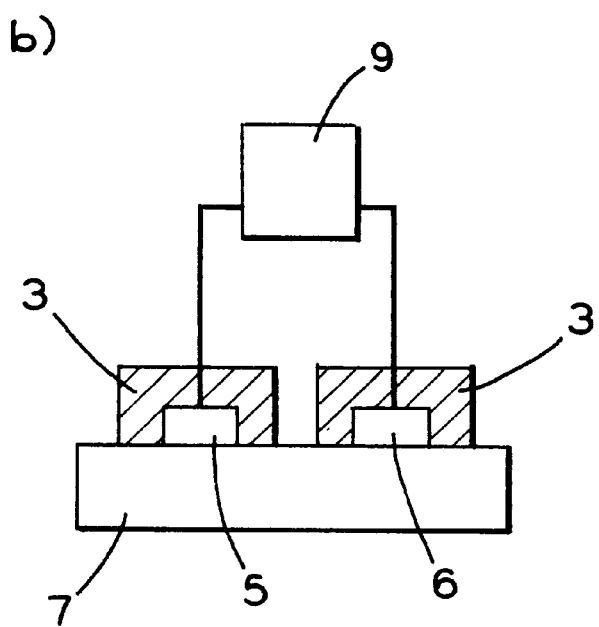

FIG. 3 shows examples of measuring arrangements consisting of a cation-selective sensor with two electrodes 5, 6 and a measuring instrument 9. With regard to the practical way in which conductive measurements are taken, distinction can be made between two basic types of measuring cells:

1. Both conductors 5, 6 are covered by the layer 3, which in this way forms a continuous bulk phase (FIG. 3a);
2. Each of the conductors 5, 6 is covered separately by the layer 3, and the layers do not form a continuous bulk phase (FIG. 3b). It is also possible for only one conductor to be covered by the layer 3.

For case 1 (see FIG. 3a), the ratio between the characteristic dimensions of the layer 3 (thickness - d) and those of the conductors 5, 6 (minimum distance between the conductors a, maximum width of the conductor along the connecting line b) may correspond to two characteristic cases:

1.1. either a or b or both are greater than d;

1.2. a and b are both less than d.

Cases 1.1 and 2 are similar in the sense that, with arrangements of this type, the change in the conductance of the tested solution, into which the sensor probe is dipped, contributes to the measured sensor output signal. Measurements of the specific ion concentration are, however, also still possible in this case if:

the background conductance of the sample is constant, the conductance of the sample is very much greater than the conductance of the cation-selective membranes used;

the sensor characteristics in a standard solution of known or adjusted conductance have been determined before and after measurement in a solution;

parallel measurements of the conductance of the sample have been taken and brought into consideration.

Case 1.2 corresponds to the situation when the contribution of the volume conductance of the sample to the sensor output signal is minimal, so that the measured signal corresponds primarily to the volume conductance of the ion-selective membrane.

The electrodes may, for example, be designed as wire electrodes. It has been found to be advantageous in this case that production is extremely straightforward and cost-efficient.

Disk electrodes have the advantage that the probe can be reconditioned simply by polishing the measuring surface of the electrodes.

Figure 4:
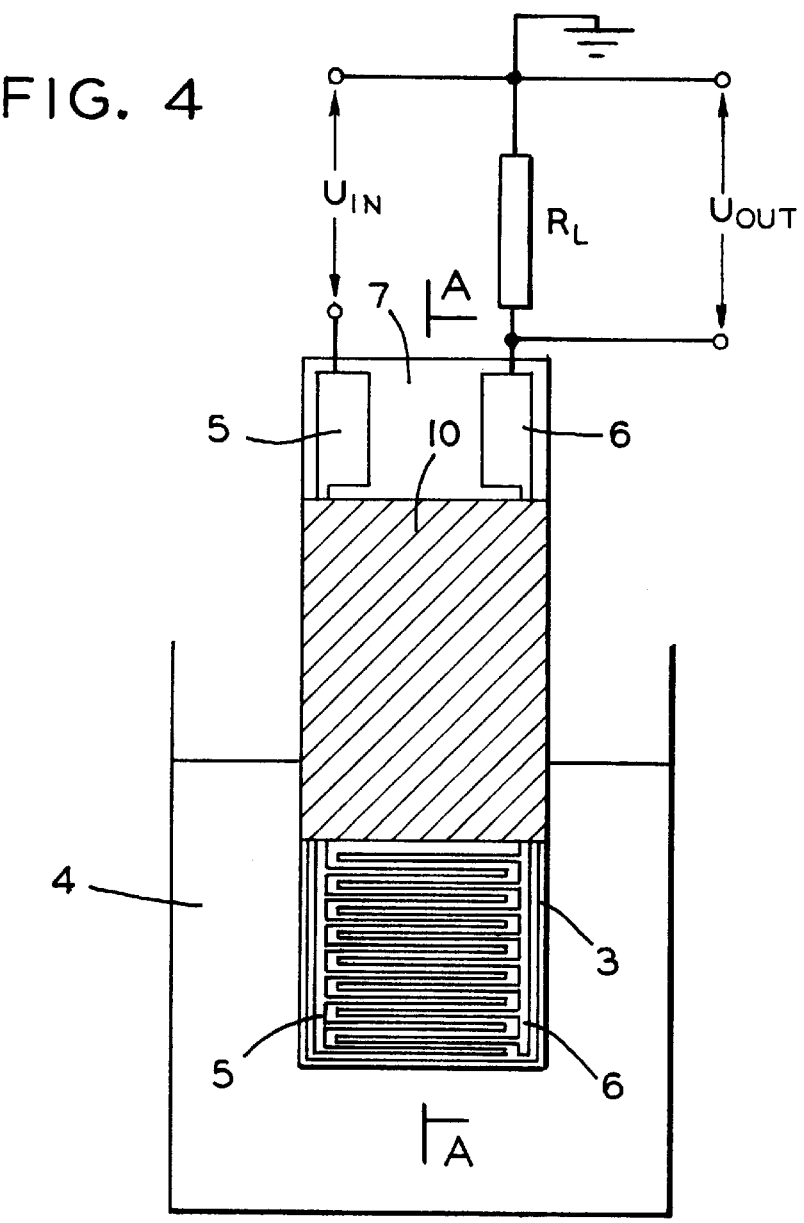
FIG. 4 schematically shows the structure of the measuring electrodes in the form of interdigital electrodes, and a measuring arrangement for measuring the admittance of the sensor.
Figure 4:
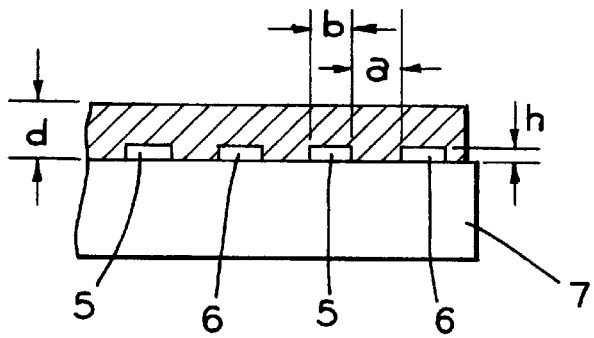

Interdigital electrodes, as represented in FIG. 4, form a preferred design possibility for the sensor electrodes.

Two interdigital electrodes (IDEs), or conduction bands, 5, 6 are applied to an insulating substrate 7 (FIG. 4). The latter may be a polymer band (for example polyimide), glass, ceramic (for example fused aluminium or sital), sapphire or passivated silicon. The electrode materials may consist of ionically conducting, electronically conducting or semiconducting materials.

The electrode regions connecting the measuring part to the contact faces of the sensor chip must be covered by an electrically insulating layer 10. The passivation layer 10 leaves only the electrical access and the sensitive area of the electrode 5, 6 uncovered. The passivation layer 10 may, for example, be a polymer film (high-temperature crosslinked polyimide or photoresists) or an inorganic film of, for example pyrolytic silicon oxide, CVD silicon nitride or applied glass.

The advantage with the use of an IDE resides in the possibility of densely arranging the electrodes (the dimensions a and b may be reduced down to the submircro-scale) while at the same time having a large periphery, which leads to an increase in the sensitivity of the conductance measurements on a small area. The lowest achievable limit for the dimensions a and b is about 0.1 $\mu$m, 2 $\mu$m or 50 $\mu$m, if electron photolithography, optical photolithography or screen-printing technology are employed for producing the electrodes. The thickness h of the electrodes is preferably in a range of from 0.01 $\mu$m to 10 $\mu$m.

The cation-selective layer 3 is applied to the measuring face of the IDE, which is free of passivation. The membrane must cover the entire sensitive area of the electrodes 5, 6. Since the electrical conductance of the ion-selective membrane is rather low (its resistance may reach a level of $10^8$ $\Omega \cdot cm^2$) even small parts of the electrode which are directly exposed to the solution prohibit reliable measurement of the membrane conductance, because the electrode resistance is less than the actual membrane resistance, and the electrode can therefore short-circuit the current in the measurement circuit.

The dimensions a, b and h should as far as possible be chosen such that the condition 1.2 (see above) is met, that is to say the membrane thickness d should be greater than a as well as b and h. The thickness of the passivation layer covering the central part of the chip should preferably be greater than that of the measurement membrane. For this case, changes in the background conductance of the sample interfere to the least extend with the measurements of the conductance of the ion-selective membrane.

The invention comprises not only single-analyte, but also multi-analyte probes which can be produced by combining or integrating multiple electrodes on one sensor unit or one support, and may be coated with layers specific to different cations. Sensors with moderate selectivity may likewise be integrated in a multisensor unit, with the result that "fingerprints" corresponding to the different compositions of the sample solution are obtained. Subsequently, using various pattern recognition methods, the relevant response patterns may be assigned a corresponding sample composition. The multisensor design which is preferred is based on the use of micro-electronic chips with the requisite number of interdigital electrode pairs, each pair being coated with the suitable membrane. A design of this type has the advantage of technological compatibility with IC technologies, as well as the fact that miniaturization is straightforward.

Conductance measurements were taken with sensors produced in accordance with the illustrative embodiments according to FIG. 1 and FIG. 2.

There are several available techniques for the measurement of material conductance, and these can be basically divided into DC and AC techniques (Cooper, W. D., Helfrick, A. D. -E., Elektrische Meßtechnik [Electrical Measurment Techniques], VCH: Weinheim, Basel, Cambridge, N.Y., 1989). The AC techniques are generally preferred since they permit a reduction in the signal-to-noise ratio and, especially in the present case of ionic conductance, prevent concentration polarization in the vicinity of the electrode surfaces.

As an alternative, measurements of the bulk conductance of layers can be taken using the bipolar pulse techniques described by Johnson, D. E. and Enke C. G., Bipolar pulse technique for fast conductance measurements, Analytical chemistry, 1970, v. 42, p. 329–335. The advantages of this technique consist in the fact that the measurements can be taken quickly (as little as 10 $\mu$s) and irrespective of parallel and series stray capacitances.

One of the simplest electrical arrangements used to measure the admittance (impedance) of the sensor and therefore the conductance of the measurement membrane is represented in FIG. 4.

The load resistor $R_L$ is connected in series with the sensor of interest, and the voltage drop across $R_L$ gives the output signal. When an AC input voltage is applied, the preferred condition for the use of an arrangement of this type is when the impedance $Z_{sensor}$ of the tested sensor is substantially greater than $R_L$ within the frequency range used for the input voltage. In this case, the current in the direction of the load resistor is primarily determined by the impedance of the sensor, and can be readily calculated using the following formula $$I(\omega) = U_{out}(\omega)/R_L \quad (1)$$

In this formula, $\omega$ is the angular frequency of the input voltage $U_{inp}$, and $U_{out}$ is the output voltage.

If an AC input voltage is applied, both the amplitude and the phase of the output signal (voltage or current) is frequency-dependent. The dispersion (frequency dependence) of the output signal is, under the conditions established above, primarily determined by the AC impedance of the sensor being tested.

The admittance of the sensor can be calculated using the following formula $$Y = \frac{\text{Re}(U_{out})}{R_L \cdot |U_{inp}|} + i \frac{\text{Im}(U_{out})}{R_L \cdot |U_{inp}|} \quad (2)$$

The first term on the right-hand side represents the real part of the sensor admittance $$\text{Re}(Y) = \frac{\text{Re}(U_{out})}{R_L \cdot |U_{inp}|} \quad (3)$$

which is proportional to the measured output signal and can be calculated using equation 3, assuming that $R_L$ and the amplitude of the input voltage $U_{imp}$ are known.

In a few measuring instruments, the impedance Z of the sensor is measured instead of its admittance Y. The impedance Z of a system represents the inverse of the associated admittance. Impedance measurements can therefore likewise be used to characterize the conductance of a measurement membrane.

In order to make it possible to monitor the changes in the membrane conductance, in the preferred embodiment of the invention, measurements of the admittance are used, or alternatively of a phase component of the output signal of the measuring arrangement in FIG. 4. These values likewise depend on frequency, and this dependence can vary in different frequency ranges. The customary operating frequency is chosen while including thee factors with the aim of optimizing the sensor response, reducing outlay in terms of the measuring arrangement and suppressing non-specific interference. The preferred working range is at frequencies of between 100 Hz and 100 kHz.

Illustrative embodiment

Two identical pairs of interdigital thin-film metal electrodes made of Ni, Pt or Au are produced by vacuum evaporation on a 0.5 mm thick ceramic substrate. The dimensions of a sensor chip are approximately 5 mm×20 mm. Each electrode finger is about 10 μm wide and about 1 mm long, with a spacing of about 10 μm between the electrode fingers of a pair. The sensitive area of an electrode pair forming each impedimetric transducer is about 1 mm². In order to limit the sensitive area of the sensor, the central part of the chip is encapsulated with a layer of Dow Corning silicone rubber. The full chip layout is represented schematically in FIG. 4.

The polymer material used in polyvinyl chloride homopolymer with high molecular weight, and the plasticizer is o-nitrophenyl octyl either. The potassium-selective coupling element used in a component known from the prior art, the natural antibiotic valynomycin. As the component with acidic and basic properties, ETH 2412, 3-hydroxy-4-(4-nitrophenolazo)phenyl octadecanoate. All the components can be obtained from the company Fluka (Buchs).

The cation-selective layer has the following composition: 5.5 mg of ETH 2412, 15 mg of valinomycin, 160 mg of o-nitrophenyl octyl either, 80 mg of PVC. This composition is dissolved in 3 ml of tetrahydrofuran and applied to the sensitive area of the transducer by dipping the sensor into this solution.

The sample solution has a universal buffer (10 nM $NaH_2PO_4$, 6.6 mM citric acid, 21.5 mM $Na_2B_4O_7$) added to it and is adjusted to a pH of 5 using dilute $H_2SO_4$.

What is claimed is:

1. Cation-selective sensor for the qualitative and/or quantitative determination of cations in solutions, characterized in that the cation-selective sensor contains at least one ionically conducting cation-specific layer which is in contact with the solution and is made of a liquid, solid or semi-solid material, in that this layer contains coupling elements which selectively remove the cations from the solution, so that the resistance, conductance, admittance or impedance of the layer is changed by cation uptake, in that the cation-specific layer contains at least one acid/base component, and in that the sensor comprises at least two electrodes, at least one of which is connected to the cation-specific layer.

2. Cation-selective sensor according to claim 1, characterized in that the acid/base component is present in the cation-specific layer in the form of functional groups with acid/base properties.

3. Cation-selective sensor according to claim 1, characterized in that the acid/base component is present in the cation-specific layer in the form of at least one chemical compound with acid/base properties.

4. Cation-selective sensor according to claim 1, characterized in that the cation-specific layer contains a component to which the acid/base component is bound.

5. Cation-selective sensor according to claim 1, characterized in that the acid/base component is lipophilic.

6. Cation-selective sensor according to claim 1, characterized in that the acid/base component is lipophilic acid or lipophilic base.

7. Cation-selective sensor according to claim 1, characterized in that the acid/base component has an acid dissociation constant $pK_a$ in the range from 3 to 12.

8. Cation-selective sensor according to claim 1, characterized in that the acid/base component has an acid dissociation constant $pK_a$ in the range from 6 to 8.

9. Cation-selective sensor according to claim 1, characterized in that the acid/base component is a pH indicator or a derivative of a pH indicator.

10. Cation-selective sensor according to claim 9, characterized in that the pH indicator or the derivative is lipophilic.

11. Cation-selective sensor according to claim 9, characterized in that the pH indicator or a derivative is lipophilically modified by the coupling of benzyl radicals or alkane chains.

12. Cation-selective sensor according to claim 9, characterized in that the acid/base component is a phenolic compound such as p-nitrophenol, a compound or a derivative of fluorescein, of a fluorescein ester, of 7-hydroxycoumarin, of resorufin, of flavone or of pyren-3-ol, or a component such as 7-(n-decyl)-2-methyl-4-(3',5'-dichlorophen-4'-one) indonaphthol.

13. Cation-selective sensor according to claim 1, characterized in that the acid/base component is fatty acid, a lipid or a surfactant.

14. Cation-selective sensor according to claim 1, characterized in that the acid/base component is 3-hydroxy-4-(4-nitrophenolazo)phenylocatadecanoate.

15. Cation-selective sensor according to claim 1, characterized in that the cation-specific layer contains at least one of the components: organic liquid, plasticizer, ion exchanger, polymer, support material or an arbitrary combination of these components.

16. Cation-selective sensor according to claim 1, characterized in that the cation-specific layer is lipophilic.

17. Cation-selective sensor according to claim 1, characterized in that the cation-specific layer has a thickness of between 0.01 μm and 1 mm.

18. Cation-selective sensor according to claim 1, characterized in that the cation-specific layer contains 20–80% by weight of polymer material, 20–80% by weight of plasticizer, 1–10% by weight of cation-selective coupling elements and 1–10% by weight of acid/base components.

19. Cation-selective sensor according to claim 18, characterized in that the cation-specific layer contains 1–10% by weight of ion exchanger.

20. Cation-selective sensor according to claim 1, characterized in that the cation-specific layer is applied to an inert support.

21. Cation-selective sensor according to claim 1, characterized in that a further layer is applied to the cation-specific layer.

22. Cation-selective sensor according to claim 21, characterized in that the further layer contains at least one soluble buffer.

23. Cation-selective sensor according to claim 21, characterized in that the further layer contains at least one component used for preparation of the cation solution to be analyzed.

24. Cation-selective sensor according to claim 21, characterized in that the further layer contains a porous support or matrix stabilizing the cation-specific layer.

25. Cation-selective sensor according to claim 21, characterized in that the individual components of the further layer are soluble in the solution and adjust the pH and/or ionic strength of the solution.

26. Cation-selective sensor according to claim 21, characterized in that the further layer has a thickness of between 0.01 μm and 1 mm.

27. Cation-selective sensor according to claim 1, characterized in that the sensor is designed as a test strip.

* * * * *